United States Patent
Fukuhara et al.

(10) Patent No.: US 10,642,245 B2
(45) Date of Patent: May 5, 2020

(54) MOTOR CONTROL DEVICE, MOTOR DEVICE, AND PROGRAM

(71) Applicant: MABUCHI MOTOR CO., LTD., Matsudo, Chiba (JP)

(72) Inventors: Kazuki Fukuhara, Chiba (JP); Kentaro Sakamoto, Chiba (JP)

(73) Assignee: MABUCHI MOTOR CO., LTD., Matsudo, Chiba (JP)

( * ) Notice: Subject to any disclaimer, the term of this patent is extended or adjusted under 35 U.S.C. 154(b) by 0 days.

(21) Appl. No.: 16/142,383

(22) Filed: Sep. 26, 2018

(65) Prior Publication Data

US 2019/0227517 A1    Jul. 25, 2019

(30) Foreign Application Priority Data

Jan. 24, 2018  (JP) ................. 2018-009468

(51) Int. Cl.
| | | |
|---|---|---|
| *G05D 23/275* | (2006.01) | |
| *G05B 19/402* | (2006.01) | |
| *A61M 5/315* | (2006.01) | |
| *H02P 29/00* | (2016.01) | |

(Continued)

(52) U.S. Cl.
CPC ....... *G05B 19/402* (2013.01); *A61M 5/31576* (2013.01); *H02P 6/16* (2013.01); *H02P 29/00* (2013.01); *H02P 29/024* (2013.01); *A61M 2005/31588* (2013.01); *A61M 2205/3317* (2013.01); *A61M 2205/3365* (2013.01);

(Continued)

(58) Field of Classification Search
CPC .. H02P 6/16; H02P 21/18; H02P 21/32; H02P 2205/01; H02P 2203/03; G05B 2219/34013
See application file for complete search history.

(56) References Cited

U.S. PATENT DOCUMENTS

| | | | |
|---|---|---|---|
| 8,206,351 | B2 | 6/2012 | Sugimoto et al. |
| 9,149,582 | B2 | 10/2015 | Sugimoto et al. |

(Continued)

FOREIGN PATENT DOCUMENTS

JP          2011005280 A       1/2011

*Primary Examiner* — Karen Masih
(74) *Attorney, Agent, or Firm* — Myers Wolin, LLC

(57) ABSTRACT

A motor control device includes: a rotational position calculator that calculates a rotational position of a motor that rotates a rotor; an operation state controller that controls a state of supply of operation power to the rotational position calculator; a deviation calculator that calculates a deviation of a rotational position of the rotor on the basis of a stop target rotational position of the rotor and the rotational position of the rotor after supply of a drive current to a coil is stopped and before supply of operation power to the rotational position calculator is stopped; a storage controller that stores the deviation on a storage; a rotational position control signal generator that generates a rotational position control signal for controlling the rotational position of the rotor on the basis of the deviation stored on the storage and the stop target rotational position of the rotor; and a drive current output unit that outputs the drive current to the coil on the basis of the rotational position control signal after supply of operation power to the rotational position calculator is restarted by the operation state controller.

8 Claims, 15 Drawing Sheets

(51) Int. Cl.
 *H02P 6/16* (2016.01)
 *H02P 29/024* (2016.01)
(52) U.S. Cl.
 CPC .............. *A61M 2205/50* (2013.01); *G05B 2219/34013* (2013.01); *H02P 2203/05* (2013.01)

(56) References Cited

U.S. PATENT DOCUMENTS

2005/0197650 A1  9/2005  Sugimoto et al.
2017/0077850 A1* 3/2017  Hamada .............. H02P 6/182

* cited by examiner

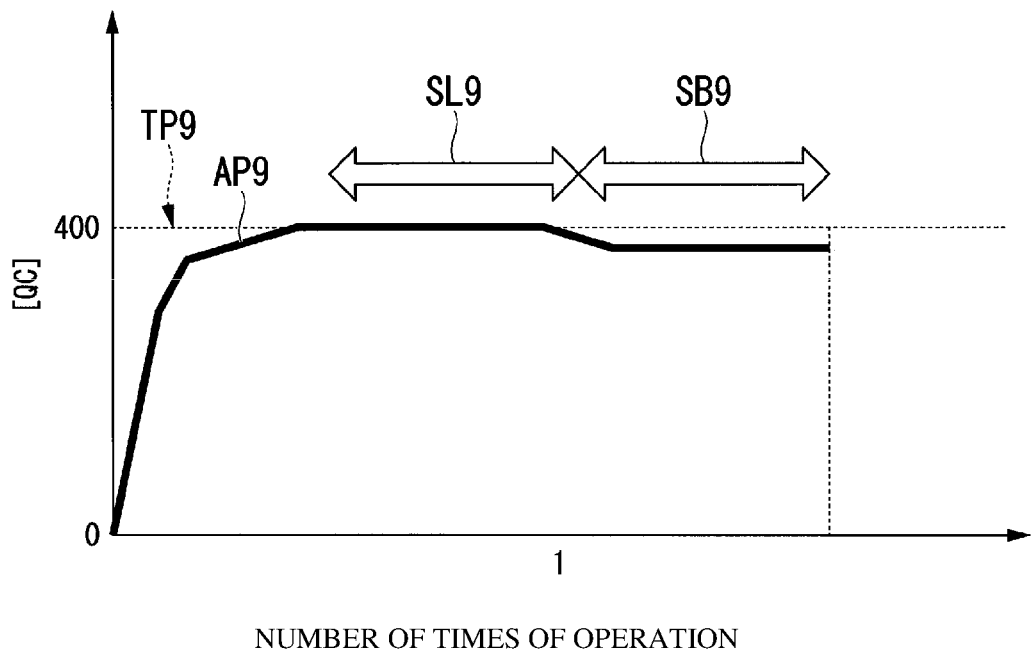
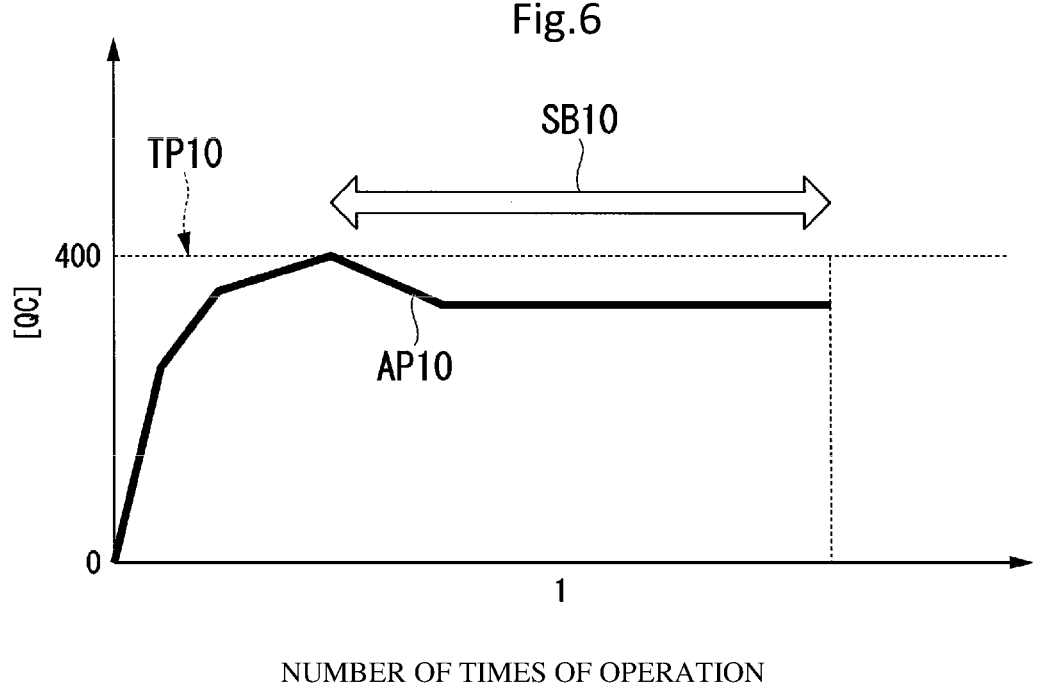

Fig.8

| NUMBER OF TIMES OF OPERATION | COMMAND PULSE [QC] | CORRECTED COMMAND PULSE [QC] | ACHIEVED PULSE [QC] | ACCUMULATED PULSE [QC] | DEVIATION [QC] |
|---|---|---|---|---|---|
| 1 | 400 | 400 | 400 | 400 | 0 |
| 2 | 400 | 400 | 380 | 780 | -20 |
| 3 | 400 | 420 | 425 | 1205 | +5 |
| 4 | 400 | 395 | 395 | 1600 | 0 |

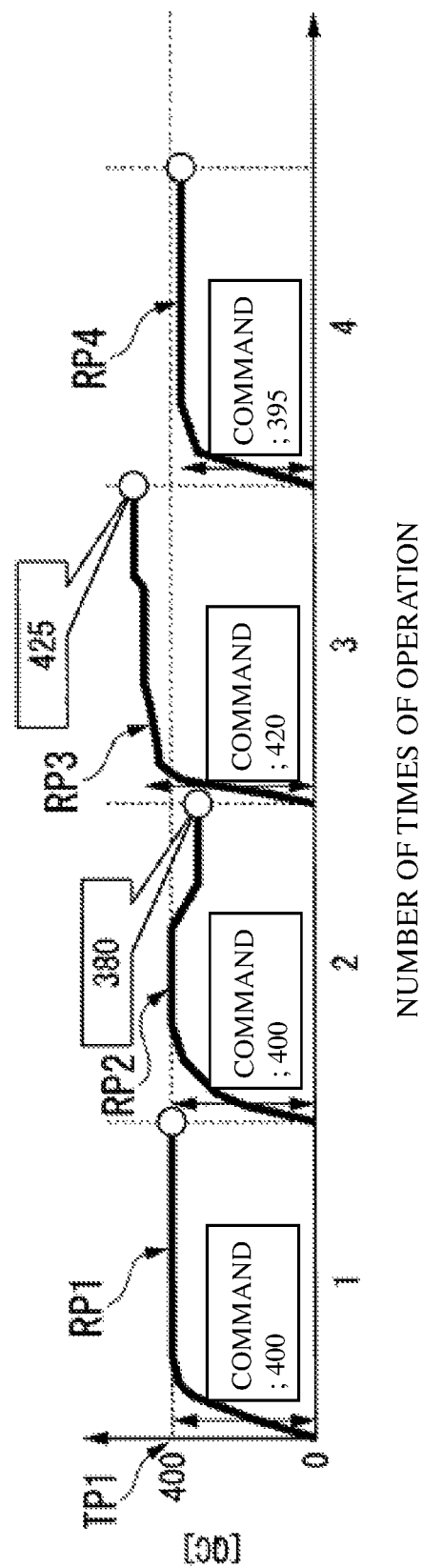

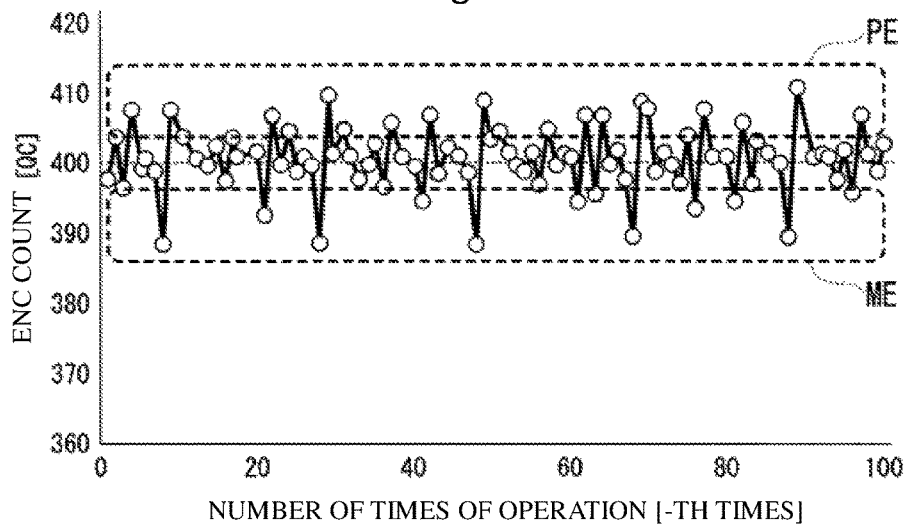

| NUMBER OF TIMES | TARGET [QC] | ACTUAL MEASUREMENT [QC] | ERROR [QC] | ERROR RATE [%] |
|---|---|---|---|---|
| MAXIMUM VALUE | 400 | 410 | +10 | 2.50 |
| AVERAGE VALUE | 400 | 400 | ±0 | ±0.00 |
| MINIMUM VALUE | 400 | 388 | −10 | −3.00 |
| TOTAL IN 20 TIMES OF OPERATION | 8000 | 8002 | +2 | +0.02 |
| TOTAL IN 100 TIMES OF OPERATION | 40000 | 40000 | ±0 | ±0.00 |

Fig.13

| SERVO LOCK IS NOT USED AND CORRECTION FUNCTION IS NOT USED | SERVO LOCK IS USED AND CORRECTION FUNCTION IS NOT USED | SERVO LOCK IS NOT USED AND CORRECTION FUNCTION IS USED | SERVO LOCK IS USED AND CORRECTION FUNCTION IS USED |
|---|---|---|---|
| 38845 | 39695 | 39999 | 40000 |

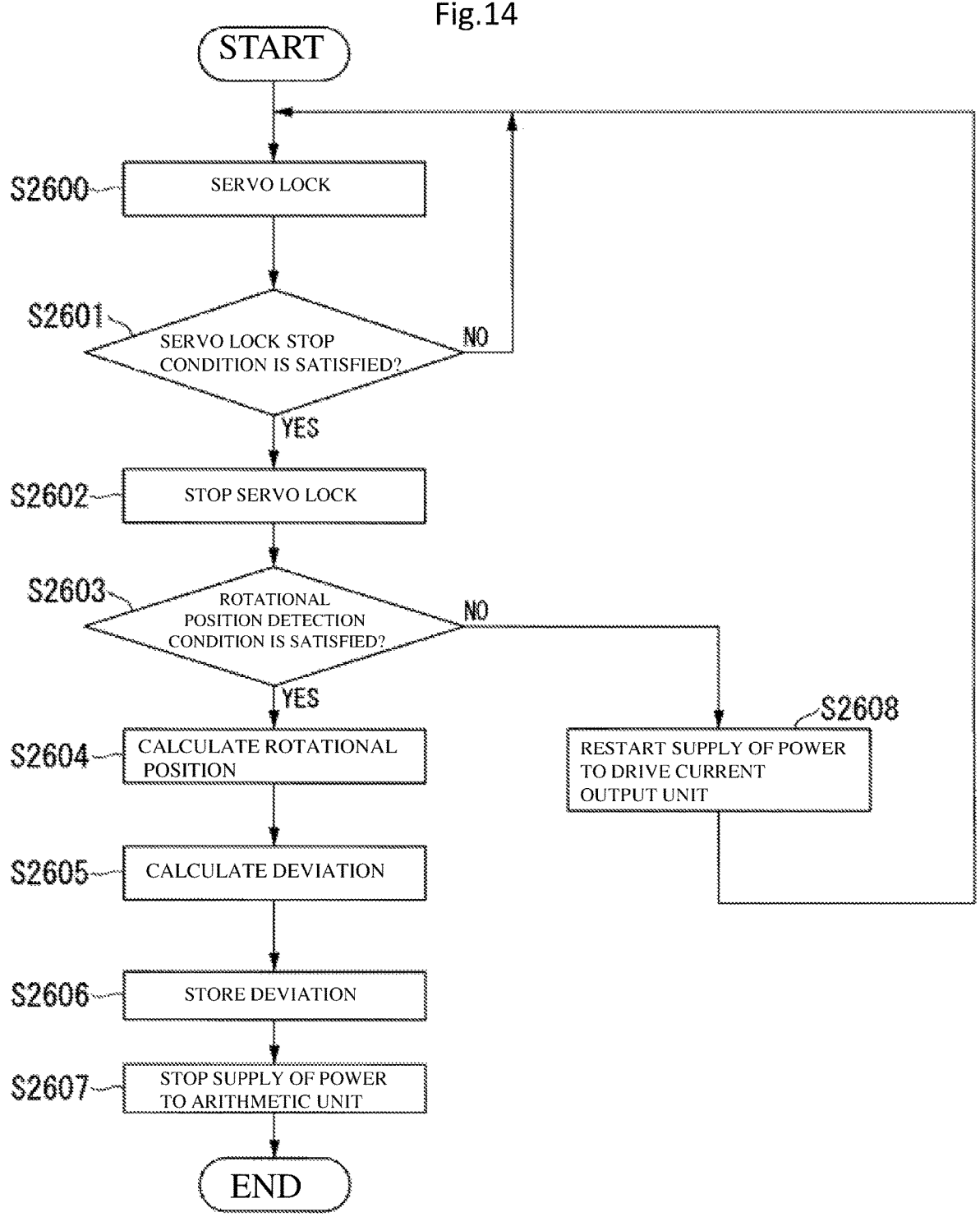

| NUMBER OF TIMES | TARGET [QC] | ACTUAL MEASUREMENT [QC] | ERROR [QC] | ERROR RATE [%] |
|---|---|---|---|---|
| MAXIMUM VALUE | 400 | 401 | +1 | 0.25 |
| AVERAGE VALUE | 400 | 393 | −7 | −1.75 |
| MINIMUM VALUE | 400 | 379 | −21 | −5.25 |
| TOTAL IN 20 TIMES OF OPERATION | 8000 | 7922 | −78 | −0.97 |
| TOTAL IN 100 TIMES OF OPERATION | 40000 | 39259 | −741 | −1.85 |

MOTOR CONTROL DEVICE, MOTOR DEVICE, AND PROGRAM

BACKGROUND

Technical Field

The present disclosure relates to a motor control device, a motor device, and a program.

In a medical medicine administration tool, it is possible to reduce a burden of medicine administration operation by electrically injecting medicine. The burden of the medicine administration operation can be reduced, whereas, in some cases, a patient feels anxious about the medicine administration tool, i.e., whether or not an electric syringe including a drive unit such as a motor normally operates. In a case where the electric syringe does not normally operate, an error in an amount of medicine to be administered occurs and appropriate treatment cannot be provided.

There is known a medical administration tool capable of reducing physical and mental distress to a patient and administering medicine in a more stable state (JP-A-2011-5280). The medical administration tool disclosed in JP-A-2011-5280 detects a dose of medicine to be administered by performing program processing on the basis of a set value of a past dose and detects a dose set by a user with the use of an electronic circuit. The medical administration tool disclosed in JP-A-2011-5280 compares the dose of the medicine to be administered with the set dose, and, in a case where the set dose is equal to or less than a predetermined value of the dose of the medicine to be administered, operates a motor and performs injection processing.

SUMMARY

In the medical administration tool disclosed in JP-A-2011-5280, a discharge device including a pump and a motor for driving the pump is used and discharges a certain amount of medicine at certain time intervals. Such a discharge device is demanded to have a high accuracy of discharge amount for appropriate treatment.

The accuracy of discharge amount is demanded in terms of not only an error in a discharge amount occurring in one time of discharge but also errors accumulated in a plurality of times of discharge. Therefore, in order to improve the accuracy of discharge amount, it is necessary to accurately control a rotational position of the motor for driving the pump and stop the motor. The medical administration tool disclosed in JP-A-2011-5280 is demanded to operate with small power consumption, and therefore, in some cases, supply of power is stopped when the medical administration tool does not perform medicine administration.

In some cases, an error in a stop position of the motor obtained in a case where supply of power is stopped occurs every time when supply of power is stopped and errors are accumulated in a plurality of times of operation. This error occurs because rotational force is generated in a rotor when the motor is stopped due to magnetic force of the motor itself, external force from a gear unit connected to the motor, and the like. For example, in a case of a cored motor, this error mainly occurs due to a cogging torque generated when the motor is stopped.

In the medical administration tool disclosed in JP-A-2011-5280, even in a case where the motor operates after the set dose is checked, a discharge amount of medicine to be actually administered is influenced by an error in the rotational position of the motor obtained when the motor is stopped.

The present disclosure has been made in view of the above points and provides a motor control device, a motor device, and a program capable of correcting an error in a rotational position of a motor after supply of power is stopped. The rotational position of the motor is a rotational position of a rotor forming the motor.

The present disclosure has been made to solve the above-mentioned problems, and an aspect of the present disclosure is a motor control device including: a rotational position calculator configured to calculate a rotational position of a motor that rotates a rotor with an interaction of magnetic force between a magnetic body around which a coil through which a drive current flows is wound and a permanent magnet; an operation state controller configured to control a state of supply of operation power to the rotational position calculator; a deviation calculator configured to calculate a deviation of a rotational position of the rotor on the basis of a stop target rotational position of the rotor and the rotational position of the rotor calculated by the rotational position calculator after supply of the drive current to the coil is stopped and before supply of operation power to the rotational position calculator is stopped by the operation state controller; a storage controller configured to store the deviation calculated by the deviation calculator on a storage after supply of the drive current to the coil is stopped; a rotational position control signal generator configured to generate a rotational position control signal for controlling the rotational position of the rotor on the basis of the deviation stored by the storage controller on the storage after supply of the drive current to the coil is stopped and the stop target rotational position of the rotor; and a drive current output unit configured to output the drive current to the coil on the basis of the rotational position control signal generated by the rotational position control signal generator after supply of operation power to the rotational position calculator is restarted by the operation state controller.

Further, as an aspect of the present disclosure, in the motor control device, the rotational position calculator calculates the rotational position when predetermined time elapses after supply of the drive current to the coil is stopped.

Further, as an aspect of the present disclosure, in the motor control device, the deviation calculator calculates the deviation in a case where a time change in the rotational position calculated by the rotational position calculator after supply of the drive current to the coil is stopped and before supply of operation power to the rotational position calculator is stopped by the operation state controller is equal to or less than a predetermined value.

Further, as an aspect of the present disclosure, in the motor control device, the deviation calculator restarts supply of the drive current to the coil in a case where the time change in the rotational position calculated by the rotational position calculator after supply of the drive current to the coil is stopped and before supply of operation power to the rotational position calculator is stopped by the operation state controller is larger than the predetermined value, and the rotational position calculator calculates the rotational position after supply of the drive current to the coil is restarted.

Further, an aspect of the present disclosure is a motor device including the above motor control device.

Further, an aspect of the present disclosure is a program for causing a computer to execute: a rotational position calculation step of calculating a rotational position of a motor that rotates a rotor with an interaction of magnetic force between a magnetic body around which a coil through which a drive current flows is wound and a permanent magnet; an operation state control step of controlling a state of supply of operation power in the rotational position calculation step; a deviation calculation step of calculating a deviation of a rotational position of the rotor on the basis of a stop target rotational position of the rotor and the rotational position of the rotor calculated in the rotational position calculation step after supply of the drive current to the coil is stopped and before supply of operation power in the rotational position calculation step is stopped in the operation state control step; a storage control step of storing the deviation calculated in the deviation calculation step on a storage after supply of the drive current to the coil is stopped; a rotational position control signal generation step of generating a rotational position control signal for controlling the rotational position of the rotor on the basis of the deviation stored on the storage after supply of the drive current to the coil is stopped in the storage control step and the stop target rotational position of the rotor; and a drive current output step of outputting the drive current to the coil on the basis of the rotational position control signal generated in the rotational position control signal generation step after supply of operation power in the rotational position calculation step is restarted by the operation state control step.

According to the present disclosure, it is possible to correct an error in a rotational position of a motor after supply of power is stopped.

BRIEF DESCRIPTION OF THE DRAWINGS

FIG. 5 illustrates an example of a rotational position in one time of operation obtained in a case where a servo lock according to the first embodiment of the present disclosure is used;

FIG. 6 illustrates an example of a rotational position in one time of operation obtained in a case where the servo lock according to the first embodiment of the present disclosure is not used;

FIG. 8 illustrates an example of correction of a command value according to the first embodiment of the present disclosure;

FIGS. 10A and 10B illustrate an example of rotational positions in the number of times of operation according to the first embodiment of the present disclosure;

FIG. 11 illustrates an example of actual measurement values of rotational positions of the motor in the number of times of operation according to the first embodiment of the present disclosure;

FIG. 12 illustrates an example of actual measurement values of errors in a rotational position of the motor according to the first embodiment of the present disclosure;

FIG. 13 illustrates an example of actual measurement values of rotational positions of the motor in each condition according to the first embodiment of the present disclosure;

FIG. 14 illustrates an example of a modification example of the stop sequence of the motor according to the first embodiment of the present disclosure;

DESCRIPTION OF THE EMBODIMENTS (Embodiment)

Figure 1:
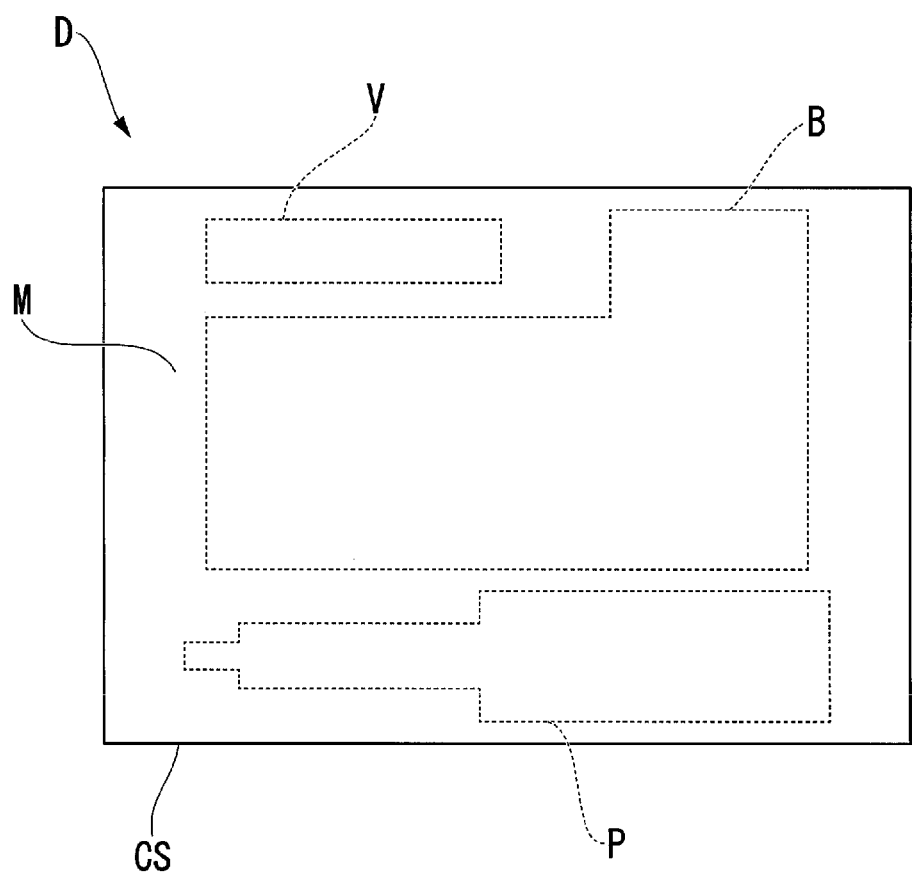
FIG. 1 illustrates an example of an external appearance of a medicine administration tool according to a first embodiment of the present disclosure.

Hereinafter, an embodiment of the present disclosure will be described in detail with reference to the drawings. FIG. 1 illustrates an example of an external appearance of a medicine administration tool D according to this embodiment. The medicine administration tool D is a portable tool for administering medicine to a patient. Administration of medicine using the medicine administration tool D is performed, for example, several times a week or several times a day.

The medicine administration tool D includes a medicine discharge unit P, a circuit board B, and a power supply V in a case CS. An operation unit M is provided on the outside of the case CS. The operation unit M accepts operation from a user, such as setting a dose of medicine of the medicine administration tool D. The circuit board B controls the medicine discharge unit P on the basis of the dose of medicine set via the operation unit M. The power supply V supplies power to the medicine administration tool D. The power supply V is, for example, a dry cell.

The medicine discharge unit P includes, for example, a motor and a syringe.

The syringe is filled with medicine. The syringe discharges medicine in accordance with rotation of the motor.

The motor includes a gear head, a motor main body, and an encoder.

The motor main body includes a rotor, a housing, a commutator, and an end bell.

The rotor includes a core, a coil, and a shaft. The motor main body is a motor that rotates the rotor with an interaction of magnetic force between a magnetic body around which the coil through which a drive current flows is wound and a permanent magnet. The motor main body is, for example, a cored motor.

The gear head is engaged with the motor main body. An output shaft of the gear head rotates once when the rotor rotates a predetermined number of times.

The encoder is a magnetic encoder as an example.

The encoder detects a rotational position of the rotor and a direction of rotation of the rotor. The encoder supplies a signal indicating the detected rotational position of the rotor and the direction of rotation of the rotor to the circuit board B. The signal indicating the rotational position of the rotor herein is, for example, the number of pulse.

Figure 2:
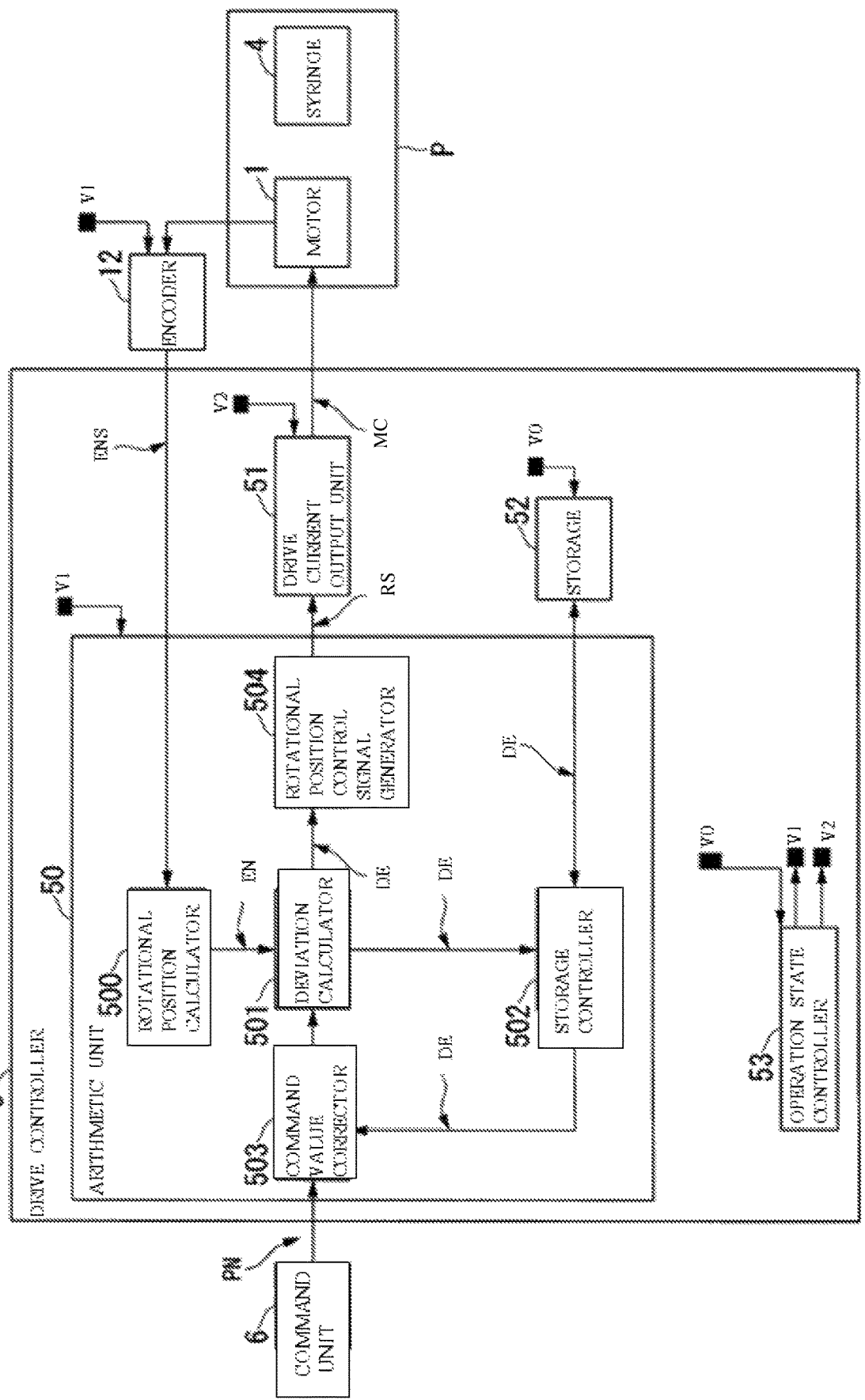
FIG. 2 illustrates an example of a configuration of a drive controller according to the first embodiment of the present disclosure.

FIG. 2 illustrates an example of a configuration of a drive controller 5 according to this embodiment. The drive controller 5 and a command unit 6 are achieved by the circuit board B of FIG. 1. The drive controller 5 includes an arithmetic unit 50, a drive current output unit 51, a storage 52, and an operation state controller 53.

The arithmetic unit 50 includes a rotational position calculator 500, a deviation calculator 501, a storage controller 502, a command value corrector 503, and a rotational position control signal generator 504.

The rotational position calculator 500 calculates a rotational position of a motor 1 on the basis of a rotational position signal ENS supplied from an encoder 12. The rotational position of the motor 1 herein is a rotational position of the rotor. The rotational position signal ENS is a signal indicating a rotational position EN of the rotor and is, for example, the number of pulse. The rotational position calculator 500 supplies the calculated rotational position EN to the deviation calculator 501.

The deviation calculator 501 calculates a deviation DE on the basis of a corrected command value DP supplied from the command value corrector 503 and the rotational position EN supplied from the rotational position calculator 500. The deviation calculator 501 supplies the calculated deviation DE to the storage controller 502 and the rotational position control signal generator 504. The deviation calculator 501 herein supplies the calculated deviation DE to the storage controller 502 and the rotational position control signal generator 504 every time when the rotational position calculator 500 supplies the rotational position EN.

Herein, an example of the deviation DE calculated by the deviation calculator 501 will be described with reference to FIG. 3.

Figure 3:
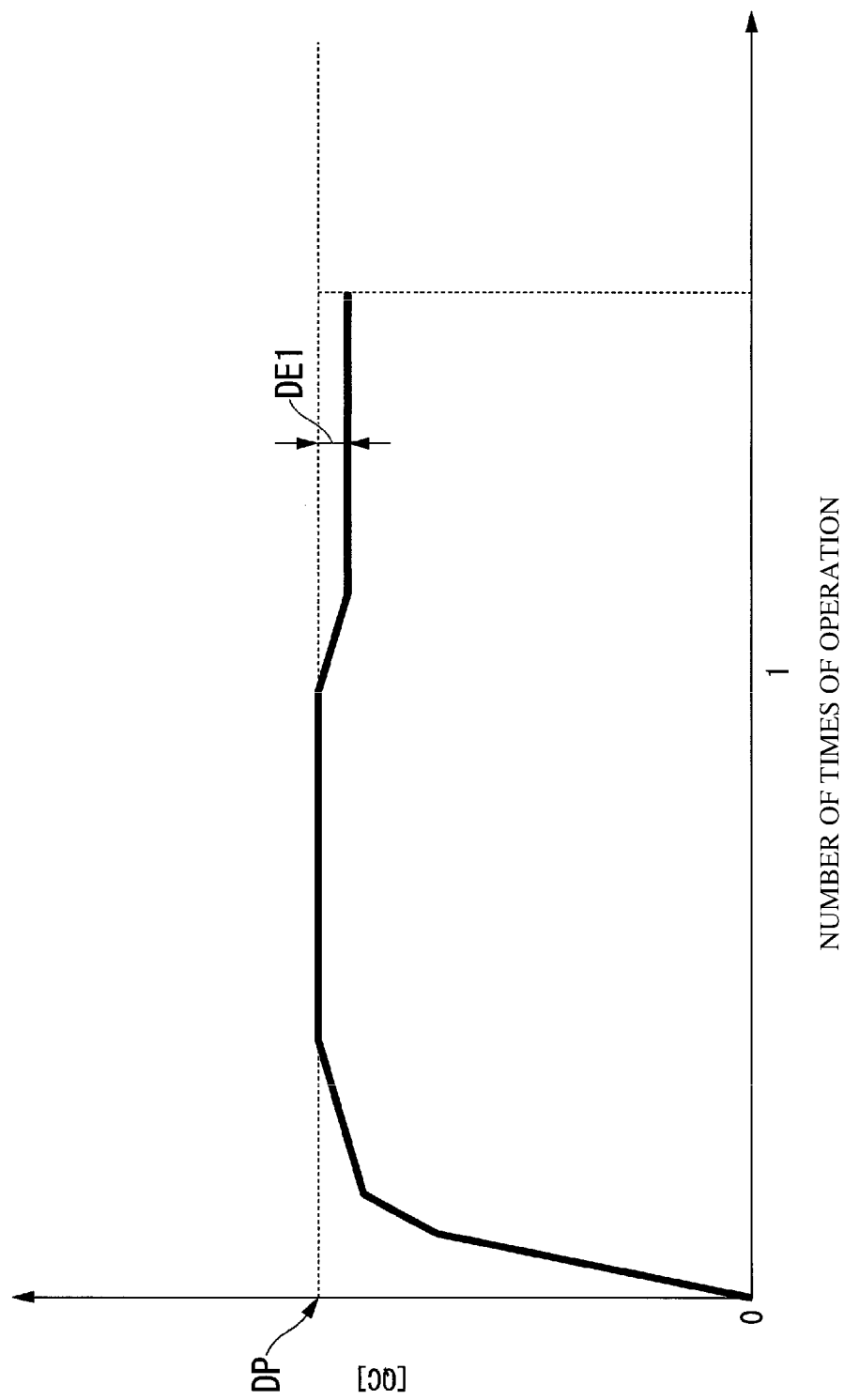
FIG. 3 illustrates an example of a deviation according to the first embodiment of the present disclosure.

FIG. 3 illustrates an example of the deviation DE according to this embodiment. The deviation DE calculated by the deviation calculator 501 is a difference between the corrected command value DP and the rotational position EN.

The corrected command value DP indicates a stop target rotational position of the rotor. The stop target rotational position of the rotor herein corresponds to a rotational position of the rotor obtained when the rotor is subjected to stop control. The stop target rotational position of the rotor is indicated by, for example, the number of pulse.

A deviation DE1 is an example of the deviation DE after supply of a drive current to the coil is stopped. The deviation DE1 is an error in the stop position of the rotor.

Note that, although a form in which the deviation DE is a difference between the corrected command value DP and the rotational position EN will be described in this embodiment, the deviation DE is not limited thereto. The deviation DE may be a difference between a rotational position at which the rotor is to rotate at each time in order to arrive at a target rotational position indicated by the corrected command value DP when the rotor stops and the rotational position EN. A value of the deviation DE1 that is the deviation DE after supply of a drive current to the coil is stopped is not changed between a case where the deviation DE is a difference between a rotational position at which the rotor is to rotate at each time in order to arrive at a target rotational position indicated by the corrected command value DP when the rotor stops and the rotational position EN and a case where the deviation DE is a difference between the corrected command value DP and the rotational position EN.

The description of the configuration of the drive controller 5 will be continued with reference to FIG. 2 again.

The storage controller 502 controls the storage 52. The storage controller 502 stores the deviation DE supplied from the deviation calculator 501 on the storage 52 after supply of a drive current to the coil is stopped. Herein, the storage controller 502 stores, on the storage 52, the last deviation DE among the deviations DE supplied from the deviation calculator 501.

Further, the storage controller 502 acquires the deviation DE stored on the storage 52 and supplies the deviation DE to the command value corrector 503. The command value corrector 503 corrects a command value PN supplied from the command unit 6 by using the deviation DE supplied from the storage controller 502. The command value PN herein is a value indicating the stop target rotational position of the rotor. The deviation DE supplied from the storage controller 502 is an error in the stop position of the rotor. In other words, the command value corrector 503 corrects the stop target rotational position of the rotor by using an error in the stop position of the rotor.

The command value corrector 503 supplies the corrected command value PN to the deviation calculator 501 as the corrected command value DP.

The rotational position control signal generator 504 generates a rotational position control signal RS on the basis of the deviation DE supplied from the deviation calculator 501. The rotational position control signal RS is a signal for controlling the rotational position of the rotor. The rotational position control signal generator 504 supplies the generated rotational position control signal RS to the drive current output unit 51.

The drive current output unit 51 generates a drive current MC on the basis of the rotational position control signal RS supplied from the rotational position control signal generator 504. The drive current output unit 51 outputs the generated drive current MC to the motor 1. Further, after supply of operation power to the rotational position calculator 500 is restarted by the operation state controller 53, the drive current output unit 51 outputs the drive current MC to the coil on the basis of the rotational position control signal RS generated by the rotational position control signal generator 504.

The deviation DE calculated by the deviation calculator 501 is stored on the storage 52. The storage 52 receives power from a power supply V0.

The operation state controller 53 controls a state of supply of operation power to the arithmetic unit 50, a state of supply of operation power to the encoder 12, and a state of supply of operation power to the drive current output unit 51. The operation state controller 53 receives power from the power supply V0. The operation state controller 53 controls a power supply V1 and a power supply V2. The power supply V1 is a power supply that supplies power to the arithmetic unit 50 and the encoder 12. Therefore, by controlling the power supply V1, the operation state controller 53 controls a state of supply of operation power to the rotational position calculator 500 included in the arithmetic unit 50. The power supply V2 is a power supply that supplies power to the drive current output unit 51.

Figure 4:
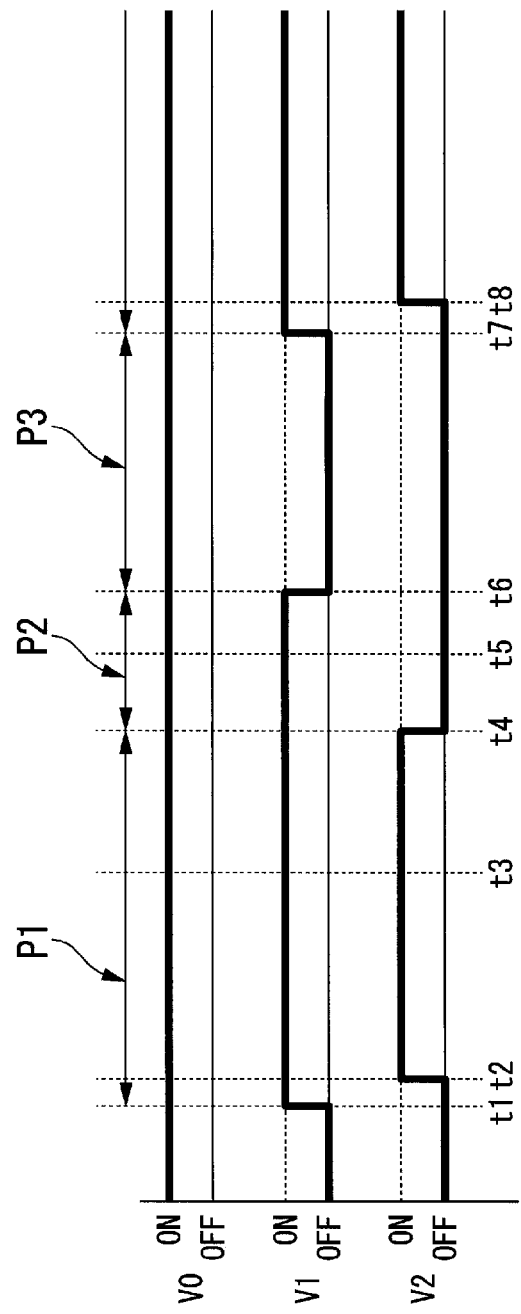
FIG. 4 illustrates an example of a section indicating a state of supply of power according to the first embodiment of the present disclosure.

Herein, the state of supply of power to the drive controller 5 and the encoder 12 will be described with reference to FIG. 4. FIG. 4 illustrates an example of a section indicating a state of supply of power according to this embodiment.

The power supply V0 constantly supplies power to the operation state controller 53 and the storage 52. The power supply V0 is the power supply V of FIG. 1.

The section indicating the state of supply of power includes three sections, i.e., a drive section P1, a stop section P2, and a sleep section P3 depending on whether the operation state controller 53 turns on or off the power supply V1 and the power supply V2.

The drive section P1 is a section in which power is supplied to the arithmetic unit 50, the encoder 12, and the drive current output unit 51. The drive section P1 is a section between a time t1 at which supply of power to the arithmetic unit 50 and the encoder 12 by the power supply V1 is started and a time t4 at which supply of power to the drive current output unit 51 by the power supply V2 is stopped. A time t2 included in the drive section P1 is a time at which supply of power to the drive current output unit 51 by the power supply V2 is started. A time t3 included in the drive section P1 is a time at which a stop sequence for stopping supply of the drive current MC to the coil is started. The stop sequence will be described below.

Medicine is discharged by the medicine discharge unit P in the drive section P1. A length of the drive section P1 is, for example, approximately several seconds.

The stop section P2 is a section in which power is supplied to the arithmetic unit 50 and the encoder 12 and power is not supplied to the drive current output unit 51. The stop section P2 is a section between the time t4 and a time t6 at which supply of power to the arithmetic unit 50 and the encoder 12 by the power supply V1 is stopped. A time t5 included in the stop section P2 is a time at which the encoder 12 detects the rotational position of the rotor after supply of the drive current MC to the coil is stopped.

A length of the stop section P2 is approximately several milliseconds.

The sleep section P3 is a section in which power is not supplied to the arithmetic unit 50, the encoder 12, and the drive current output unit 51. The sleep section P3 is a section between the time t6 and a time t7 at which supply of power to the arithmetic unit 50 and the encoder 12 by the power supply V1 is started. When supply of power to the arithmetic unit 50 and the encoder 12 by the power supply V1 is started, supply of power to the drive current output unit 51 by the power supply V2 is started at a time t8.

The sleep section P3 is determined in accordance with an interval of medicine administration. A length of the sleep section P3 is, for example, approximately several hours.

The description of the configuration of the drive controller 5 will be continued with reference to FIG. 2 again.

The command unit 6 supplies the command value PN to the command value corrector 503. The command unit 6 calculates the command value PN on the basis of the dose of medicine set via the operation unit M of FIG. 1.

The encoder 12 detects the rotational position of the rotor of the motor 1 and the direction of rotation of the rotor and generates the rotational position signal ENS on the basis of the detected result. The encoder 12 supplies the generated rotational position signal ENS to the rotational position calculator 500.

The motor 1 is driven when the drive current MC supplied from the drive controller 5 flows through the coil. When the motor 1 is driven, a syringe 4 discharges medicine.

Herein, the error in the stop position of the rotor will be described.

FIG. 5 illustrates an example of the rotational position in one time of operation obtained in a case where a servo lock according to this embodiment is used. The servo lock herein has a function of holding the stop position of the rotor. When the rotor rotates from the stop position for one pulse due to external force, the servo lock causes the drive current MC to flow through the coil to generate a torque having an opposite direction to the external force and holds the stop position of the rotor.

The servo lock is controlled by the drive controller 5. In a state in which the drive controller 5 causes the servo lock to be active, power is supplied to the arithmetic unit 50 from the power supply V1 and power is supplied to the drive current output unit 51 from the power supply V2. In the servo lock, the arithmetic unit 50 generates the rotational position control signal RS for generating a torque having an opposite direction to external force on the basis of the rotational position signal ENS supplied from the encoder 12. The drive current output unit 51 causes the drive current MC to flow through the coil on the basis of the rotational position control signal RS generated by the arithmetic unit 50.

When a rotational position AP9 of the rotor arrives at a target position TP9, the drive controller 5 activates the servo lock in a servo lock section SL9. The target position TP9 is a rotational position indicated by the command value PN supplied from the command unit 6. When a condition for releasing the servo lock is satisfied, the servo lock is released. The drive controller 5 causes the operation state controller 53 to stop supply of power to the drive current output unit 51 from the power supply V2, thereby releasing the servo lock.

When the servo lock is released, short brake works the rotor in a short brake section SB9. The short brake herein is a mechanism that short-circuits the coil of the motor 1 and applies braking force based on induced power of the motor 1 to the rotor, thereby stopping rotation.

In the example illustrated in FIG. 5, after the rotor is stopped in the short brake section SB9, the error in the stop position occurs between the rotational position AP9 and the target position TP9.

The error in the stop position of the rotor is generated due to a cogging torque or force received from the gear head. The cogging torque is a torque that is generated due to an interaction of magnetic force between the magnetic body around which the coil is wound and the permanent magnet in a state in which the drive current MC is stopped. The force received from the gear head is force that is generated due to backlash between gears and force that is pushed back from the syringe.

The error in the stop position of the rotor is accumulated when operation is repeated and becomes a large error.

FIG. 6 illustrates an example of the rotational position in one time of operation obtained in a case where the servo lock according to this embodiment is not used. In the example illustrated in FIG. 6, after the rotor is stopped, the error in the stop position occurs between a rotational position AP10 and a target position TP10 in a short brake section SB10.

Note that, although a case where short brake is used as an example will be described in this embodiment, the short brake does not need to be used.

Figure 7:
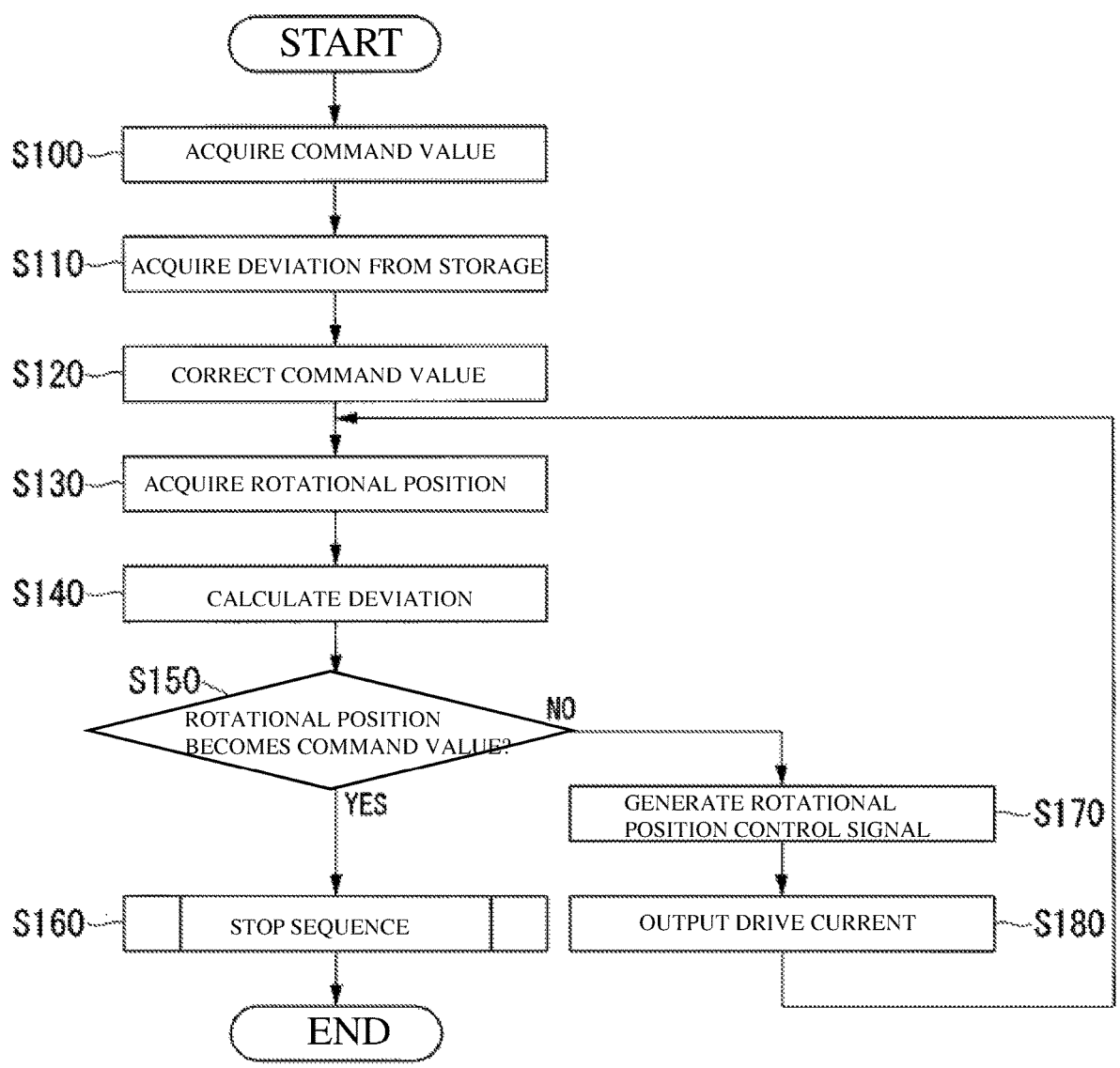
FIG. 7 illustrates an example of rotational position control processing of a motor according to the first embodiment of the present disclosure.

FIG. 7 illustrates an example of rotational position control processing of the motor 1 according to this embodiment. The processing illustrated in FIG. 7 is started in a case where time to administer medicine comes and supply of power to the drive controller 5, the command unit 6, and the encoder 12 is started.

Step S100: The command value corrector 503 acquires the command value PN supplied by the command unit 6. Note that a pulse indicated by the command value PN supplied by the command unit 6 is not changed depending on the number of times of operation of the medicine discharge unit P in this embodiment.

Step S110: The command value corrector 503 acquires the deviation DE stored on the storage 52 from the storage controller 502.

Step S120: The command value corrector 503 corrects the command value PN on the basis of the acquired deviation DE. The command value corrector 503 supplies the corrected command value PN to the deviation calculator 501 as the corrected command value DP.

Herein, correction processing of the command value PN performed by the command value corrector 503 will be described with reference to FIG. 8.

FIG. 8 illustrates an example of correction of the command value PN according to this embodiment. For example, a command pulse indicated by the command value PN in the first operation is 400 quad count (QC). The corrected command value DP, in other words, the corrected command pulse is a value obtained by the command value corrector 503 correcting the command pulse indicated by the command value PN by using the deviation DE. However, the command pulse is not corrected in the first operation, and therefore the corrected command value DP is equal to the command pulse indicated by the command value PN. An achieved pulse indicates the rotational position of the rotor obtained when the medicine discharge unit P terminates the first operation. An accumulated pulse is the number of pulse obtained by adding values of the achieved pulses in the number of times of past operation. The deviation DE is a difference between the corrected command value DP and the achieved pulse. The deviation DE is an error in the stop position of the rotor. The deviation DE has a positive value in a case where the achieved pulse is larger than the corrected command value DP. The deviation DE has a negative value in a case where the achieved pulse is smaller than the corrected command value DP.

The command value corrector 503 sets a value obtained by subtracting the deviation DE in the last operation from the command pulse indicated by the command value PN as the corrected command value DP.

The description of the rotational position control processing of the motor 1 will be continued with reference to FIG. 7 again.

Step S130: The rotational position calculator 500 acquires the rotational position signal ENS supplied by the encoder 12. The rotational position calculator 500 calculates the rotational position EN of the rotor on the basis of the acquired rotational position signal ENS as the number of pulse. The rotational position calculator 500 supplies the calculated rotational position EN to the deviation calculator 501.

Step S140: The deviation calculator 501 calculates the deviation DE on the basis of the corrected command value DP supplied from the command value corrector 503 and the rotational position EN supplied from the rotational position calculator 500. The deviation calculator 501 supplies the calculated deviation DE to the storage controller 502 and the rotational position control signal generator 504.

The storage controller 502 acquires the deviation DE supplied by the deviation calculator 501 but does not store the acquired deviation DE on the storage 52 while the drive current MC is being supplied to the coil.

Step S150: The deviation calculator 501 determines whether or not the rotational position EN becomes the command value PN. The deviation calculator 501 acquires the rotational position EN supplied by the rotational position calculator 500 and compares the acquired rotational position EN with the corrected command value DP. Based on the comparison result, the deviation calculator 501 determines whether or not the rotational position EN has arrived at a rotational position indicated by the corrected command value DP.

In a case where the deviation calculator 501 determines that the rotational position EN has arrived at the rotational position indicated by the corrected command value DP (Step S150; YES), the deviation calculator 501 supplies, to the drive controller 5, a signal showing that the rotational position EN has arrived at the rotational position indicated by the corrected command value DP. Thereafter, the drive controller 5 executes processing in Step S160. On the contrary, in a case where the deviation calculator 501 determines that the rotational position EN has not arrived at the rotational position indicated by the corrected command value DP (Step S150; NO), the deviation calculator 501 executes processing in Step S170.

Step S160: The drive controller 5 starts processing of the stop sequence. Herein, the stop sequence will be described with reference to FIG. 9.

Figure 9:
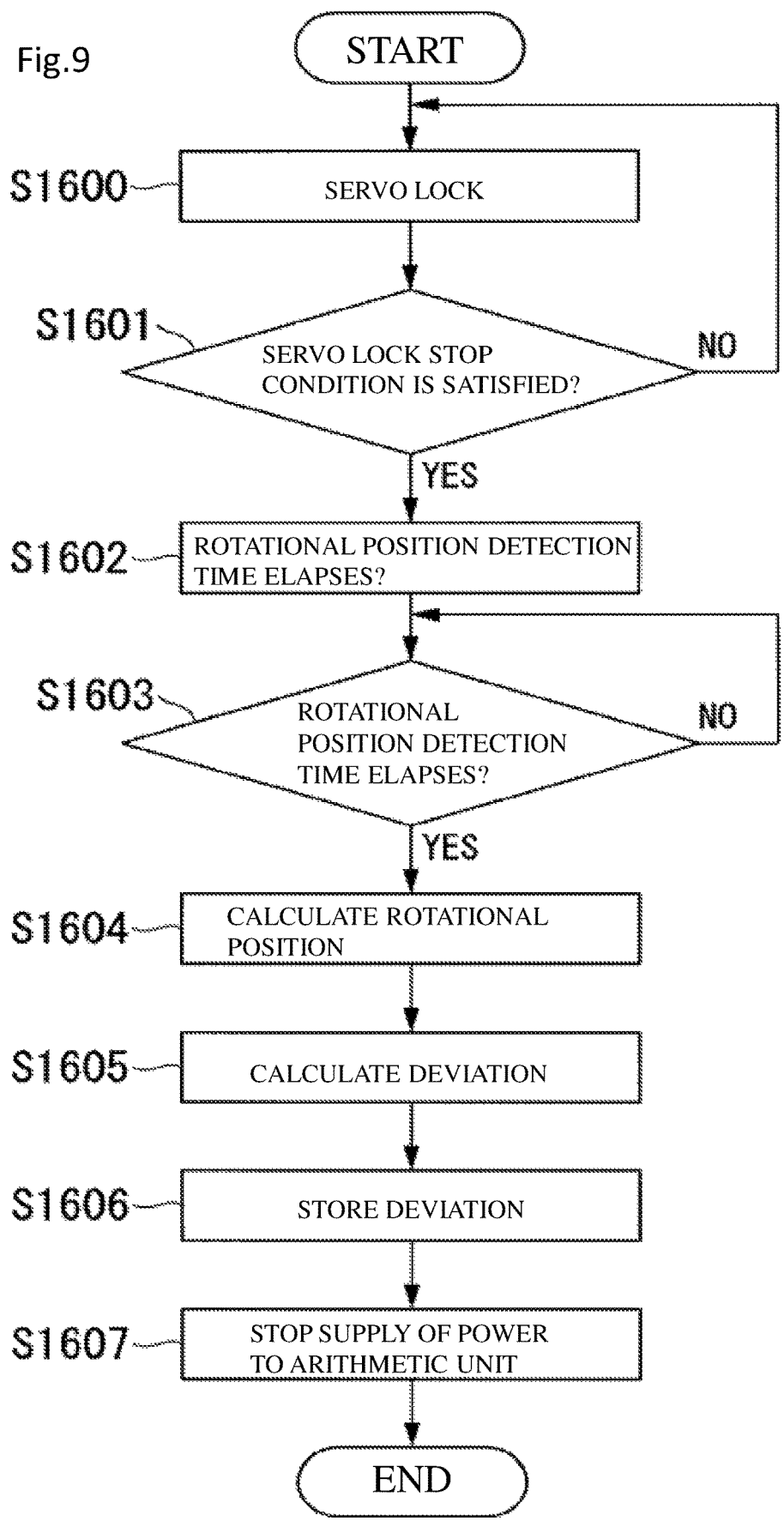
FIG. 9 illustrates an example of a stop sequence of the motor according to the first embodiment of the present disclosure.

FIG. 9 illustrates an example of the stop sequence of the motor 1 according to this embodiment.

Step S1600: The drive controller 5 activates the servo lock.

Step S1601: The drive controller 5 determines whether or not a servo lock stop condition has been satisfied. The servo lock stop condition herein is that predetermined time elapses after the rotational position of the rotor arrives at the rotational position indicated by the corrected command value DP. The predetermined time herein is 100 milliseconds as an example.

In a case where the drive controller 5 determines that the servo lock stop condition has been satisfied (Step S1601; YES), the drive controller 5 executes processing in Step S1602. On the contrary, in a case where the drive controller 5 determines that the servo lock stop condition has not been satisfied (Step S1601; NO), the drive controller 5 repeats the processing in Step S1600.

Note that, although a case where the servo lock stop condition is that predetermined time elapses after the rotational position of the rotor arrives at the rotational position indicated by the corrected command value DP will be described as an example in this embodiment, the servo lock stop condition is not limited thereto.

The servo lock stop condition may be, for example, a condition that predetermined time elapses after power is supplied to the medicine discharge unit P. The predetermined time herein is determined by, for example, measuring time until the rotational position of the rotor arrives at the rotational position indicated by the corrected command value DP in advance.

Further, the servo lock stop condition may be, for example, a condition that the drive current MC is equal to or less than a predetermined value. The servo lock stop condition may be a condition that a load of the motor 1 in one time of operation of the medicine discharge unit P is equal to or more than a predetermined value. The servo lock stop condition may be a condition that displacement of the rotational position of the rotor in one time of operation of the medicine discharge unit P is equal to or more than a predetermined number of pulse. The servo lock stop condition may be a condition that rotation speed of the rotor is equal to or less than a predetermined value.

Step S1602: The drive controller 5 stops the servo lock. The operation state controller 53 stops supply of power to the drive current output unit 51 from the power supply V2.

Step S1603: The rotational position calculator 500 determines whether or not rotational position detection time has elapsed. The rotational position detection time herein is predetermined time measured after supply of power to the drive current output unit 51 is stopped.

In a case where the rotational position calculator 500 determines that the rotational position detection time has elapsed (Step S1603; YES), the rotational position calculator 500 executes processing in Step S1604. On the contrary, in a case where the rotational position calculator 500 determines that the rotational position detection time has not elapsed (Step S1603; NO), the rotational position calculator 500 repeats the processing in Step S1603.

Step S1604: The rotational position calculator 500 calculates the rotational position EN on the basis of the rotational position signal ENS supplied by the encoder 12. In other words, the rotational position calculator 500 calculates the rotational position EN of the rotor when predetermined time elapses after supply of the drive current MC to the coil is stopped. The rotational position calculator 500 supplies the calculated rotational position EN to the deviation calculator 501.

Step S1605: The deviation calculator 501 calculates the deviation DE on the basis of the corrected command value DP supplied from the command value corrector 503 and the rotational position EN supplied from the rotational position calculator 500.

In other words, the deviation calculator 501 calculates the deviation DE on the basis of the corrected command value DP and the rotational position EN of the rotor calculated by the rotational position calculator 500 after supply of the drive current MC to the coil is stopped and before supply of operation power to the rotational position calculator 500 is stopped by the operation state controller 53. The deviation calculator 501 supplies the calculated deviation DE to the storage controller 502 and the rotational position control signal generator 504 every time when the rotational position calculator 500 supplies the rotational position EN.

Step S1606: The storage controller 502 stores the deviation DE supplied from the deviation calculator 501 on the storage 52. In other words, the storage controller 502 stores the deviation DE calculated by the deviation calculator 501 on the storage 52 after supply of the drive current MC to the coil is stopped.

Step S1607: The operation state controller 53 stops supply of power to the arithmetic unit 50 from the power supply V1. The operation state controller 53 stops supply of power to the encoder 12 from the power supply V1. The drive controller 5 stops operation until the next medicine administration time.

Herein, Step S1605 and Step S1606 in FIG. 9 will be compared with Step S140 in FIG. 7. In Step S140 of FIG. 7, the drive current MC is supplied to the coil, and the deviation calculator 501 calculates the deviation DE every time when the rotational position EN is supplied from the rotational position calculator 500. However, in Step S140 of FIG. 7, the storage controller 502 does not store the deviation DE calculated by the deviation calculator 501 on the storage 52.

On the contrary, in Step S1605 and Step S1606 of FIG. 9, the deviation calculator 501 calculates the deviation DE after supply of the drive current MC to the coil is stopped and before supply of power to the arithmetic unit 50 from the power supply V1 is stopped. The storage controller 502 stores the deviation DE calculated by the deviation calculator 501 on the storage 52. In other words, in Step S1606, the deviation DE that the storage controller 502 stores on the storage 52 is the last deviation DE calculated by the deviation calculator 501 before supply of power to the arithmetic unit 50 from the power supply V1 is stopped.

The description of the rotational position control processing of the motor 1 will be continued with reference to FIG. 7 again.

Step S170: The rotational position control signal generator 504 generates the rotational position control signal RS on the basis of the deviation DE supplied from the deviation calculator 501. The deviation DE herein is the deviation DE that is calculated by the deviation calculator 501 on the basis of the stop target rotational position of the rotor and the rotational position EN of the rotor calculated by the rotational position calculator 500 after supply of the drive current MC to the coil is stopped and before supply of operation power to the rotational position calculator 500 is stopped by the operation state controller 53 and is stored by the storage controller 502 on the storage 52 after supply of the drive current MC to the coil is stopped. In other words, the rotational position control signal generator 504 generates the rotational position control signal RS for controlling the rotational position EN of the rotor on the basis of the deviation DE stored by the storage controller 502 on the storage 52 after supply of the drive current MC to the coil is stopped and the stop target rotational position of the rotor.

The rotational position control signal generator 504 supplies the generated rotational position control signal RS to the drive current output unit 51.

Step S180: The drive current output unit 51 generates the drive current MC on the basis of the rotational position control signal RS supplied from the rotational position control signal generator 504. The drive current output unit 51 outputs the generated drive current MC to the motor 1.

Hereinafter, the number of revolutions of the rotor obtained as a result of operation of the motor 1 will be described with reference to FIGS. 10A to 14.

Figure 10A:
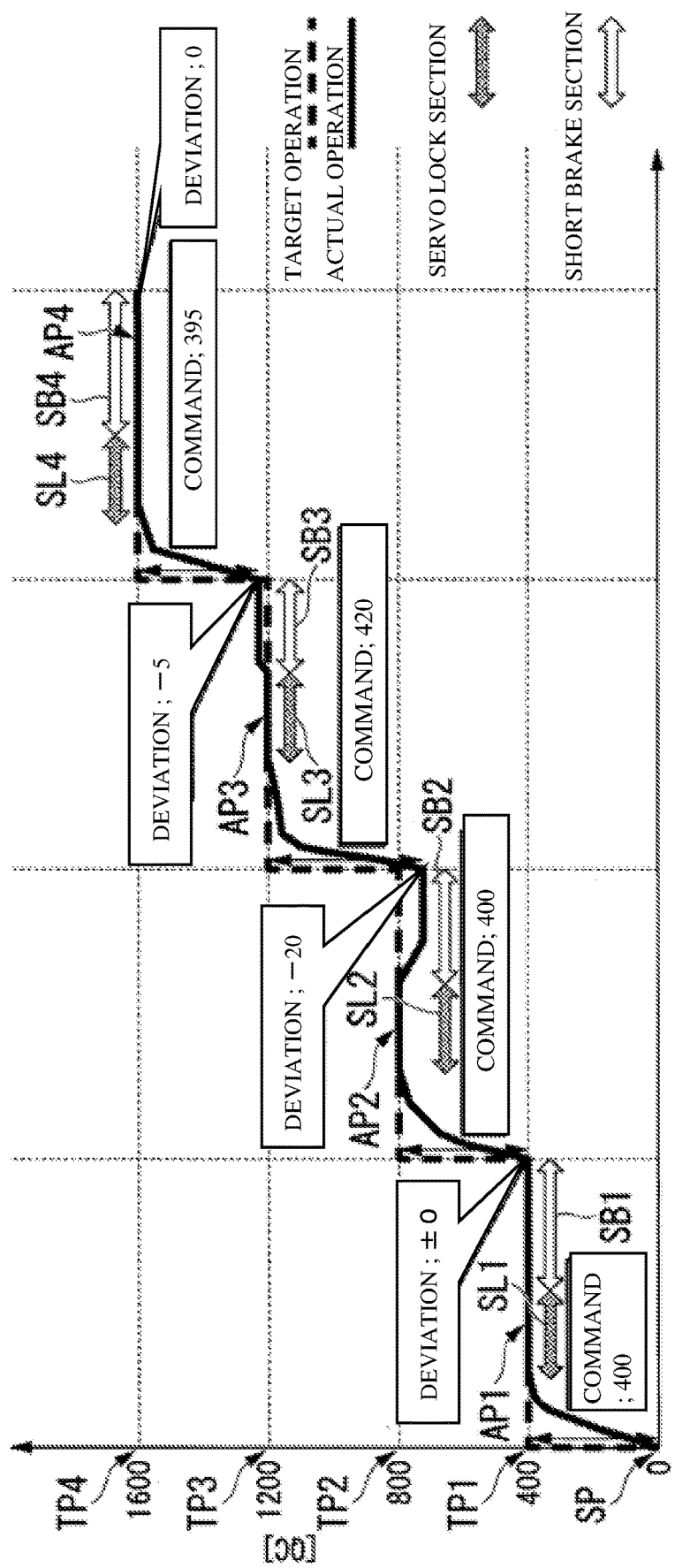

FIGS. 10A and 10B illustrate an example of the rotational positions EN in the number of times of operation according to this embodiment. In FIG. 10A, a rotational position AP1 to a rotational position AP4 are rotational positions EN of the rotor from a start position SP. Displacement of the stop position of the rotor can be read from FIG. 10A.

In FIG. 10B, each of rotational positions RP1 to RP4 is a rotational position EN of the rotor from the target number of revolutions in the last operation. For example, the rotational position RP1 is a rotational position EN of the rotor from the start position SP, and the rotational position RP2 is a rotational position EN of the rotor from a target position TP1 in the first operation. An error in the stop position of the rotor in each operation can be read from FIG. 10B.

The example of FIG. 10A shows that the error in the stop position of the rotor is not accumulated in a case where the number of times of operation is increased.

A result obtained in a case of conventional control of the motor will be described with reference to FIGS. 15A and 15B for comparison.

Figure 15A:
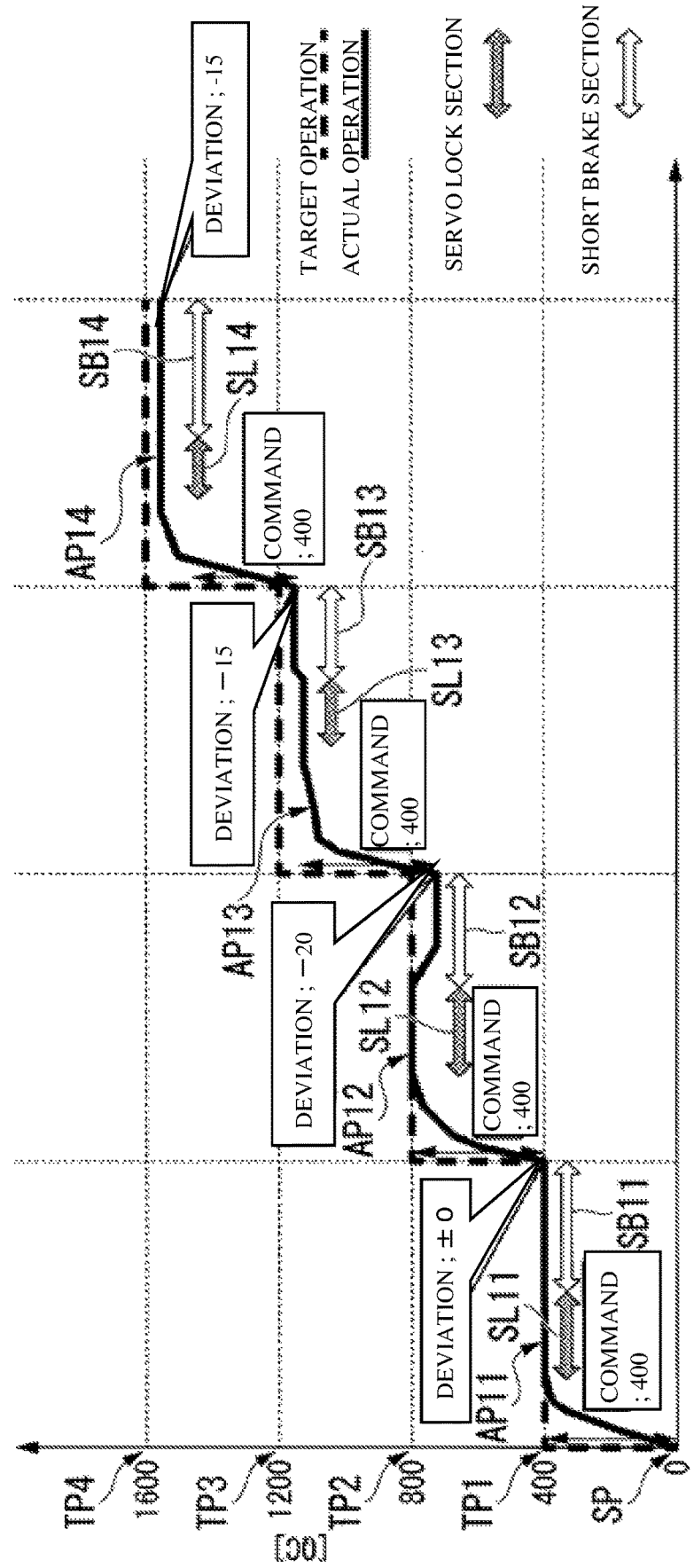
FIGS. 15A and 15B illustrate an example of rotational positions of a motor in the number of times of operation in a related art.
Figure 15B:
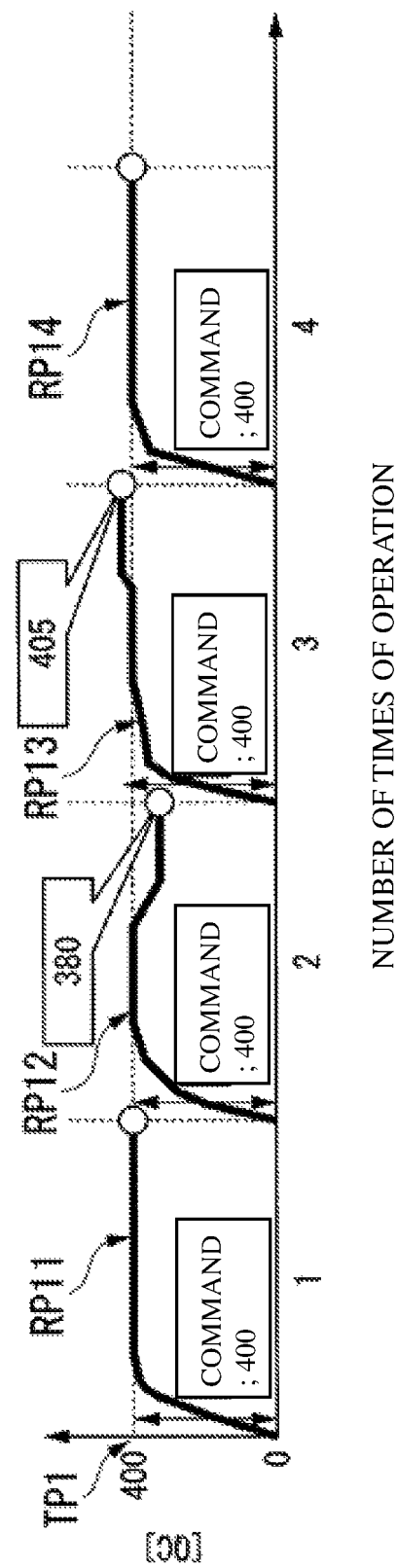

FIGS. 15A and 15B illustrate an example of the rotational positions of the motor in the number of times of operation in a related art. It is found from FIG. 15B that an error in the stop position of the rotor from the target position TP does not occur in the first operation and the fourth operation and the error in the stop position of the rotor from the target position TP occurs in the second operation and the third operation. When referring to FIG. 15B, the error in the stop position of the rotor does not occur in the fourth operation. However, when referring to FIG. 15A, the errors in the stop position of the rotor in the second operation and the third operation are accumulated, and therefore an error in the stop position of the rotor from the start position SP (−15 QC) occurs in the fourth operation.

FIG. 11 illustrates an example of actual measurement values of the rotational positions EN of the motor 1 in the number of times of operation according to this embodiment. The example illustrated in FIG. 11 shows actual measurement values of the rotational positions of the motor 1 in a hundred times of operation obtained in a case where the target position is 400 QC. In the example illustrated in FIG. 11, the servo lock is active for 100 milliseconds when drive of the motor 1 is stopped. In a case where the deviation DE having a negative value is generated in the rotational position EN of the motor 1, the number of revolutions indicated by the command value PN is corrected to have a value obtained by subtracting the deviation DE having the negative value. In other words, the number of revolutions indicated by the command value PN is corrected by adding a positive value. On the contrary, in a case where the deviation DE having a positive value is generated in the rotational position EN of the motor 1, the number of revolutions indicated by the command value PN is corrected to have a value obtained by subtracting the deviation DE having the positive value.

Therefore, in a case where the actual measurement values of the rotational position of the motor 1 fall within a rotational position range ME that is lower than the target position or fall within a rotational position range PE that is higher than the target position, the actual measurement values are corrected to be close to 400 QC serving as the target position.

FIG. 12 illustrates an example of actual measurement values of errors in the rotational position EN of the motor 1 according to this embodiment. An error rate in a hundred times of operation is 0.00 percent. There is no error in the stop position of the rotor.

A result obtained in a case of conventional control of the motor will be described with reference to FIG. 16 and FIG. 17 for comparison.

Figures 16, 17:
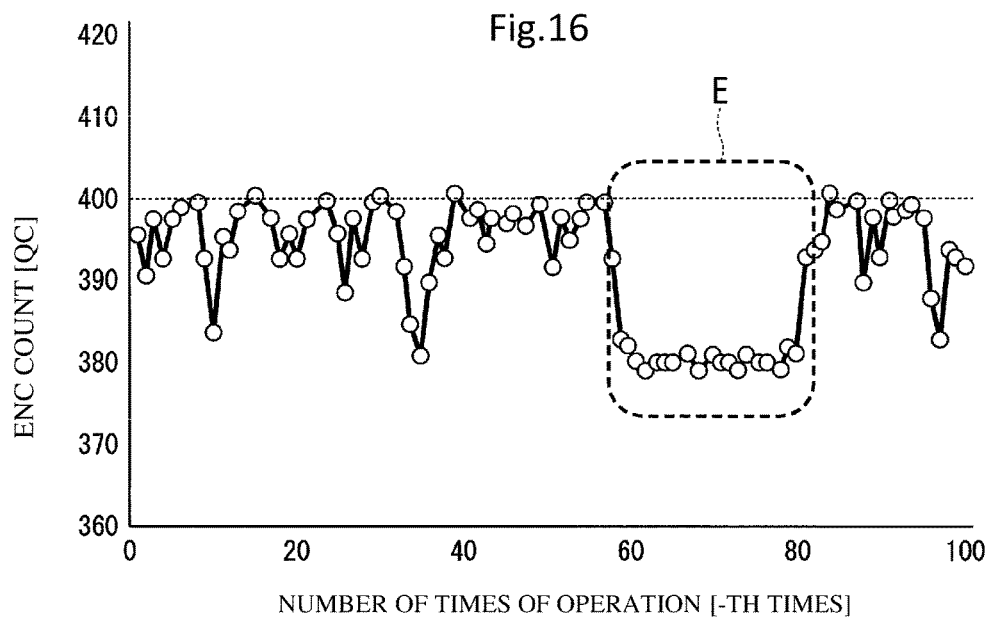
FIG. 16 illustrates an example of actual measurement values of rotational positions of a motor in the number of times of operation in a related art.
FIG. 17 illustrates an example of actual measurement values of errors in a rotational position of a motor in a related art.

FIG. 16 illustrates an example of actual measurement values of rotational positions of a motor in the number of times of operation in a related art. In the example illustrated in FIG. 16, an operation condition of the motor is the same operation condition of the motor 1 illustrated in FIG. 12 and FIG. 13 except that a command value is not corrected. The actual measurement values of the rotational positions of the motor in the number of times of operation of 60 times to 80 times fall within a rotational position range E that is lower than the target position.

FIG. 17 illustrates an example of actual measurement values of errors in the rotational position of the motor in the related art. The error rate in a hundred times of operation is −1.85 percent. In the related art, there is an error in the stop position of the rotor.

FIG. 13 illustrates an example of actual measurement values of the rotational positions EN of the motor 1 in each condition according to this embodiment. In FIG. 13, a target rotational position in one time of operation is 400 QC, and operation is performed a hundred times, and a target rotational position in a hundred times of operation is 40000 QC. The actual measurement values of the rotational positions EN of the motor 1, which are obtained in a case where the servo lock is used and the command value PN is corrected, in a case where the servo lock is used and the command value PN is not corrected, in a case where the servo lock is not used and the command value PN is corrected, and in a case where the servo lock is not used and the command value PN is not corrected, are shown as four types of samples.

When the target rotational position of 40000 QC is compared with each actual measurement value, the deviation DE of the actual measurement value from the target rotational position is smaller in a case where the command value is corrected by using the servo lock and in a case where the command value PN is corrected without using the servo lock than in a case where only the servo lock is used.

(Conclusion) As described above, the motor drive device (drive controller 5) according to this embodiment includes the rotational position calculator 500, the operation state controller 53, the deviation calculator 501, the storage controller 502, the rotational position control signal generator 504, and the drive current output unit 51.

The rotational position calculator 500 calculates the rotational position EN of the motor 1 that rotates the rotor with an interaction of magnetic force between the magnetic body around which the coil through which the drive current MC flows is wound and the permanent magnet.

The operation state controller 53 controls the state of supply of operation power to the rotational position calculator 500.

The deviation calculator 501 calculates the deviation DE of the rotational position of the rotor on the basis of the stop target rotational position of the rotor and the rotational position EN of the rotor calculated by the rotational position calculator 500 after supply of the drive current MC to the coil is stopped and before supply of operation power to the rotational position calculator 500 is stopped by the operation state controller 53.

The storage controller 502 stores the deviation DE calculated by the deviation calculator 501 on the storage 52 after supply of the drive current MC to the coil is stopped.

The rotational position control signal generator 504 generates a rotational position control signal for controlling the rotational position EN of the rotor on the basis of the deviation DE stored by the storage controller 502 on the storage 52 after supply of the drive current MC to the coil is stopped and the stop target rotational position of the rotor.

The drive current output unit 51 outputs the drive current MC to the coil on the basis of the rotational position control signal RS generated by the rotational position control signal generator 504 after supply of operation power to the rotational position calculator 500 is restarted by the operation state controller 53.

Note that, also before supply of the drive current MC to the coil is stopped, the deviation calculator 501 calculates the deviation DE every time when the rotational position EN is supplied from the rotational position calculator 500. Therefore, the deviation DE that the storage controller 502 stores on the storage 52 is the last deviation DE calculated by the deviation calculator 501 before supply of operation power (power from power supply V1) to the rotational position calculator 500 is stopped.

With this configuration, the motor drive device (drive controller 5) according to this embodiment can calculate the deviation DE on the basis of the stop target rotational position of the rotor and the rotational position EN of the rotor calculated by the rotational position calculator 500 after supply of the drive current MC to the coil is stopped and before supply of operation power to the rotational position calculator 500 is stopped by the operation state controller 53. This makes it possible to correct an error in the rotational position EN of the motor 1 from the target rotational position after supply of power is stopped.

Further, in the motor drive device (drive controller 5) according to this embodiment, the rotational position calculator 500 calculates the rotational position of the rotor when predetermined time elapses after supply of the drive current MC to the coil is stopped.

With this configuration, in the motor drive device (drive controller 5), it is possible to easily specify when the deviation DE is calculated.

Note that, in the above-mentioned embodiment, there has been described a form in which the deviation calculator 501 calculates the deviation DE between the corrected command value DP obtained by the command value corrector 503 correcting the command value PN and the rotational position EN calculated by the rotational position calculator 500. However, the present disclosure is not limited thereto. The arithmetic unit 50 does not need to include the command value corrector 503, and the deviation calculator 501 may acquire the deviation DE stored on the storage 52 from the storage controller 502, correct the command value PN by using the acquired deviation DE, and set the corrected command value DP.

(Modification Example) FIG. 14 illustrates an example of a modification example of the stop sequence of the motor 1 according to this embodiment. Processing in Step S2600 to Step S2602 and Step S2604 to Step S2607 of FIG. 14 are similar to the processing in Step S1600 to Step S1602 and Step S1604 to Step S1607 of FIG. 9, respectively, and therefore description thereof will be omitted.

Step S2603: The rotational position calculator 500 determines whether or not a rotational position detection condition has been satisfied. The rotational position detection condition herein is, for example, a condition that rotation speed of the rotor calculated by the rotational position calculator 500 is equal to or less than a predetermined value.

In a case where the rotational position calculator 500 determines that the rotational position detection condition has been satisfied (Step S2603; YES), the rotational position calculator 500 executes processing in Steps S2604 and S2605. In other words, the deviation calculator 501 calculates the deviation DE obtained in a case where a time change in the rotational position EN of the rotor calculated by the rotational position calculator 500 after supply of the drive current MC to the coil is stopped and before supply of operation power to the rotational position calculator 500 is stopped by the operation state controller 53 is equal to or less than a predetermined value.

On the contrary, in a case where the rotational position calculator 500 determines that the rotational position detection condition has not been satisfied (Step S2603; NO), the rotational position calculator 500 executes processing in Step S2608.

Step S2608: The operation state controller 53 restarts supply of power to the drive current output unit 51 from the power supply V2. In other words, in a case where the time change in the rotational position EN of the rotor calculated by the rotational position calculator 500 after supply of the drive current MC to the coil is stopped and before supply of operation power to the rotational position calculator 500 is stopped by the operation state controller 53 is larger than the predetermined value, the deviation calculator 501 restarts supply of the drive current MC to the coil. Thereafter, the drive controller 5 repeats the processing in Step S2600 to Step S2603. In a case where the rotational position detection condition is satisfied in Step S2603, the rotational position calculator 500 executes the processing in Step S2604. In other words, the rotational position calculator 500 calculates the rotational position EN of the rotor after supply of the drive current MC to the coil is restarted.

In the motor drive device (drive controller 5) in this modification example, the deviation calculator 501 calculates the deviation DE obtained in a case where the time change in the rotational position EN of the rotor calculated by the rotational position calculator 500 after supply of the drive current MC to the coil is stopped and before supply of operation power (power from the power supply V1) to the rotational position calculator 500 is stopped by the operation state controller 53 is equal to or less than the predetermined value. Then, the storage controller 502 stores the deviation DE supplied from the deviation calculator 501 on the storage 52. In other words, the storage controller 502 stores the deviation DE calculated by the deviation calculator 501 on the storage 52 after supply of the drive current MC to the coil is stopped.

Note that, also before supply of the drive current MC to the coil is stopped, the deviation calculator 501 calculates the deviation DE every time when the rotational position EN is supplied from the rotational position calculator 500. Therefore, the deviation DE that the storage controller 502 stores on the storage 52 is the last deviation DE calculated by the deviation calculator 501 before supply of operation power (power from the power supply V1) to the rotational position calculator 500 is stopped.

With this configuration, in the motor drive device (drive controller 5) in this modification example, it is possible to securely calculate the deviation DE after speed of the rotor is sufficiently reduced.

Further, in the motor drive device (drive controller 5) in this modification example, in a case where the time change in the rotational position EN of the rotor calculated by the rotational position calculator 500 is larger than the predetermined value after supply of the drive current MC to the coil is stopped and before supply of operation power (power from the power supply V1) to the rotational position calculator 500 is stopped by the operation state controller 53, the deviation calculator 501 restarts supply of the drive current MC to the coil, and the rotational position calculator 500 calculates the rotational position EN of the rotor after supply of the drive current MC to the coil is restarted.

With this configuration, in the motor drive device (drive controller 5) in this modification example, it is possible to prevent a timing to calculate the deviation DE from being missed because a condition that speed of the rotor is sufficiently reduced is not satisfied.

Note that part of the drive controller 5 in the above-mentioned embodiment, for example, the arithmetic unit 50, the drive current output unit 51, and the operation state controller 53 may be achieved by a computer. In that case, the part of the drive controller 5 may be achieved by recording a program for achieving this control function on a computer readable recording medium and causing a computer system to read the program recorded on this recording medium and execute the program. Note that the "computer system" herein is a computer system included in the drive controller 5 and includes hardware such as an OS and peripherals. Further, the "computer readable recording medium" indicates a portable medium such as a flexible disk, a magneto-optical disk, a ROM, and a CD-ROM and a storage device such as a hard disk included in the computer system. The "computer readable recording medium" may also include a recording medium that dynamically holds a program for a short time, such as a line of communication used in a case where the program is transmitted via a network such as the Internet or a communication line such as a telephone line, and a recording medium that holds the program for a certain time, such as a volatile memory included in a computer system serving as a server or client in that case. Further, the above-mentioned program may be a program for achieving part of the function described above and may also be a program that can achieve the function described above in combination with the program already recorded on the computer system.

Further, part of or the whole drive controller 5 in the above-mentioned embodiment may be achieved as an integrated circuit such as a large scale integration (LSI). Each functional block of the drive controller 5 may individually serve as a processor or part of or all the functional blocks may be integrated to serve as a processor. Further, a method of integrating a circuit is not limited to an LSI and may be achieved by a dedicated circuit or a general processor. Further, in a case where a semiconductor technology progresses and a technology of integrating a circuit substituted for an LSI is developed, an integrated circuit provided by using the technology may be used.

Hereinabove, an embodiment of this disclosure has been described in detail with reference to the drawings. However, a specific configuration is not limited to the configuration described above, and various design changes and the like can be made without deviating from the gist of the present disclosure.

What is claimed is:

1. A motor control device comprising:
    a rotational position calculator configured to calculate a rotational position of a motor that rotates a rotor with an interaction of magnetic force between a magnetic body around which a coil through which a drive current flows is wound and a permanent magnet;
    an operation state controller configured to control a state of supply of operation power to the rotational position calculator;
    a deviation calculator configured to calculate a deviation of a rotational position of the rotor based on a stop target rotational position of the rotor and the rotational position of the rotor calculated by the rotational position calculator after supply of the drive current to the coil is stopped and before supply of operation power to the rotational position calculator is stopped by the operation state controller;
    a storage controller configured to store the deviation calculated by the deviation calculator on a storage after supply of the drive current to the coil is stopped;
    a rotational position control signal generator configured to generate a rotational position control signal for controlling the rotational position of the rotor based on the deviation stored by the storage controller on the storage after supply of the drive current to the coil is stopped and the stop target rotational position of the rotor; and
    a drive current output unit configured to output the drive current to the coil based on the rotational position control signal generated by the rotational position control signal generator after supply of operation power to the rotational position calculator is restarted by the operation state controller.

2. The motor control device according to claim 1, wherein the rotational position calculator calculates the rotational position when predetermined time elapses after supply of the drive current to the coil is stopped.

3. The motor control device according to claim 1, wherein the deviation calculator calculates the deviation in a case where a time change in the rotational position calculated by the rotational position calculator after supply of the drive current to the coil is stopped and before supply of operation power to the rotational position calculator is stopped by the operation state controller is equal to or less than a predetermined value.

4. The motor control device according to claim 3, wherein:
    the deviation calculator restarts supply of the drive current to the coil in a case where the time change in the rotational position calculated by the rotational position calculator after supply of the drive current to the coil is stopped and before supply of operation power to the rotational position calculator is stopped by the operation state controller is larger than the predetermined value; and
    the rotational position calculator calculates the rotational position after supply of the drive current to the coil is restarted.

5. A motor device comprising the motor control device according to claim 1.

6. The motor control device according to claim 2, wherein the deviation calculator calculates the deviation in a case where a time change in the rotational position calculated by the rotational position calculator after supply of the drive current to the coil is stopped and before supply of operation power to the rotational position calculator is stopped by the operation state controller is equal to or less than a predetermined value.

7. A non-transitory computer-readable medium storing a program for causing a computer to execute:
    a rotational position calculation step of calculating a rotational position of a motor that rotates a rotor with an interaction of magnetic force between a magnetic body around which a coil through which a drive current flows is wound and a permanent magnet;
    an operation state control step of controlling a state of supply of operation power in the rotational position calculation step;
    a deviation calculation step of calculating a deviation of a rotational position of the rotor based on a stop target rotational position of the rotor and the rotational position of the rotor calculated in the rotational position calculation step after supply of the drive current to the coil is stopped and before supply of operation power in the rotational position calculation step is stopped in the operation state control step;
    a storage control step of storing the deviation calculated in the deviation calculation step on a storage after supply of the drive current to the coil is stopped;
    a rotational position control signal generation step of generating a rotational position control signal for controlling the rotational position of the rotor based on the deviation stored on the storage after supply of the drive current to the coil is stopped in the storage control step and the stop target rotational position of the rotor; and
    a drive current output step of outputting the drive current to the coil based on the rotational position control signal generated in the rotational position control signal generation step after supply of operation power in the rotational position calculation step is restarted by the operation state control step.

8. The motor control device according to claim 6, wherein:
    the deviation calculator restarts supply of the drive current to the coil in a case where the time change in the rotational position calculated by the rotational position calculator after supply of the drive current to the coil is stopped and before supply of operation power to the rotational position calculator is stopped by the operation state controller is larger than the predetermined value; and the rotational position calculator calculates the rotational position after supply of the drive current to the coil is restarted.

\* \* \* \* \*